United States Patent [19]
Gasiorek

[11] Patent Number: 5,035,845
[45] Date of Patent: Jul. 30, 1991

[54] POWDER PRESSING METHOD

[75] Inventor: Slawomir Gasiorek, Kane, Pa.

[73] Assignee: KZK Powder Technologies Corporation, Middleburg Hts., Ohio

[21] Appl. No.: 486,869

[22] Filed: Mar. 1, 1990

Related U.S. Application Data

[63] Continuation-in-part of Ser. No. 193,733, May 13, 1988, abandoned.

[51] Int. Cl.$^5$ .............................................. B29C 43/02
[52] U.S. Cl. .................................. 264/40.1; 264/109; 419/66
[58] Field of Search ...................... 264/40.1, 109, 123; 419/66

[56] References Cited

U.S. PATENT DOCUMENTS

| | | | |
|---|---|---|---|
| 3,255,716 | 6/1966 | Knochel et al. | 264/109 |
| 3,499,144 | 3/1970 | Juillet et al. | 264/109 |
| 4,100,598 | 7/1978 | Stiel et al. | 264/109 |

OTHER PUBLICATIONS

Gasiorek et al., "Mathematical Description of the Process of Compacting Ceramic Powders" Energy & Ceramics, Proceedings of the 4th International Meeting on Modern Ceramics Technologies, Saint-Vincent, Italy May 1979, pp. 223-236.

Van Grenou "Density Variations In Die-Compacted Powders" Science of Ceramics, vol. 10, pp. 93-99, 1979.

Primary Examiner—Mary Lynn Theisen

[57] ABSTRACT

This invention relates to compacts obtained from non-metallic and metallic powders by die pressing. In particular, it describes an improved method of manufacturing parts from powders where the properties of powders and green compacts can be readily controlled and modified to obtain final products according to desired specifications and dimensions. Introduction of an uniform procedure for determination of powder and green compact properties: slide coefficient, compactibility coefficient and cohesiveness, by a simple compaction test allows to optimize the selection of binders, plasticizers, lubricating substances and the methods of powder preparation prior to pressing operation. With the powder properties known, the pressing parameters can be precisely established and an optimum material and surface treatment for the compacting die can be chosen. With the value of cohesiveness given by the test, the process can be designed to eliminate mechanical defects in compacts such as cracks and laminations.

13 Claims, 1 Drawing Sheet

POWDER PRESSING METHOD

This is a continuation-in-part of application Ser. No. 07/193,733, filed May 13, 1988, now abandoned.

REFERENCES CITED—PUBLICATIONS

"Mathematical Description of the Process of Compacting Ceramic Powders", S. Gasiorek et al., *Energy and Ceramics*, in Proc. 4th Int. Meeting on Modern Ceramics Technoligies, Saint-Vincent, Italy, May 1979.

Van Grenou, Conf. Proc., *Science of Ceramics*, vol. 10, Berchtesgaden, West Germany, 1979.

BACKGROUND OF THE INVENTION

1. Field of the Invention

This invention relates to compacts obtained from nonmetallic and metallic powders through die pressing. In particular, the invention relates to an improved method of manufacturing parts from powders where the properties of powders and green compacts can be readily controlled and modified to obtain final products according to desired specifications and dimensions.

2. Discussion of the Prior Art

Powder pressing consists of compacting dry loose powder in a rigid die at sufficiently high pressures so that a dense and strong piece is formed. Depending on the mix used and production life required, dies are made from hardened steel, abrasion resistant alloys, tungsten carbide or others. Automatic dry pressing of ceramics has been practiced since 1904. The technology, originally developed for steatite porcelains that are soft, flow easily and cause little die wear, has been adopted for many kinds of ceramics and powder metallurgy. Components made from powdered materials are typically produced to final shapes, without or with very little machining required. Such products achieve high tolerances, good surface finish and uniformity in shape.

The main drawback of a die pressing is nonuniform density distribution throughout the compact. The friction between a powder and a die's wall and between all individual powder particles creates a diffusion of pressure during compaction and, as a result, variations in density. On the other hand, high quality of a final product requires the density in a compact to be as uniform as possible. The factors affecting the density distributions are: the type of compacting technique, the type of tools used, and the properties of a powder to be pressed. Therefore, for a given compacting technique and a given tool design and material, the density distribution throughout a compact depends only on powder properties.

Among the most important powder parameters are: flow rate of a loose powder, bulk density (a packing characteristic of powder grains), friction coefficient between a powder and a die's wall, and compactibility coefficient.

The flow rate and bulk density are used to estimate the efficiency of a compacting process which is restricted by the time interval needed to fill up a die with a powder in an automated process. The coefficient of friction is of crucial importance to the technical side of the compacting process. It depends on the powder properties, the material of the die, and the quality of the die surfaces. Its magnitude characterizes the powder's capability for uniform densification along a height of a compact. The compactibility coefficient is assumed to depend on powder properties (such as interparticle friction) and may be treated as a measure of the powder capability to be compacted.

At the present time there are commonly used methods for determining the bulk density and the flow rate of powders but no reliable method exists for determining the friction coefficient and the compactibility coefficient. Many studies have been carried out to express in a mathematical form the distribution of the pressing forces in dies as a function of related properties and relationships during the compacting process. The most interesting relationship derived for one-end pressing of cylindrical samples is given by Ballhausen. It can be generalized for arbitrary samples of constant cross-section as, $$p_c/p_d = \exp(u \cdot \tan \phi \cdot SH/F) \quad (1)$$

Here,
- $p_c$—pressure applied to the top punch,
- $p_d$—pressure transmitted to the bottom punch,
- $u$—friction coefficient
- $\phi$—angle of a pressure transmission from the top punch to the die's wall,
- $S$—perimeter of the cross-section of the sample,
- $H$—height of the sample.

The magnitudes of $p_c$, $p_d$, $S$, $H$, and $F$ in (1) can be easily measured. In order to determine the friction coefficient, $u$, it is necessary to correctly estimate the angle $\phi$ of the pressure transmission from the top punch to the die's walls. As yet, no reliable method has been proposed for determination of $\phi$ and thus an accurate friction coefficient $u$ cannot be obtained. As seen in the relation (1), the magnitude of the friction coefficient can vary over a wide range.

A similar approach to the above is used by Gasiorek (see Gasiorek et al.) who gives the following empirically established relationship, $$p_d/p_c = \eta^{SH/4F} \quad (2)$$

Here,
- $p_c$—pressure applied to the top punch,
- $p_d$—pressure transmitted to the bottom punch,
- $S$—perimeter of the cross-section of the sample,
- $H$—height of the sample.
- $\eta$—slide coefficient.

The slide coefficient $\eta$ characterizes interactions between the powder and the die's walls. For a given material and surface conditions of a die, the coefficient $\eta$ is a constant and describes the powder's ability to be uniformly densified during compaction. Its numerical value can vary in the range $0 < \eta < 1$.

The relation (2) allows one to calculate the slide coefficient and is of great practical importance. Comparing equations (1) and (2) it is seen that the slide coefficient and the friction coefficient are related, that is, $$\eta = \exp(-4 \cdot u \cdot \tan \phi) \quad (3)$$

Numerous experiments (see Gasiorek et al.) with various cylindrical samples subjected to a wide range of technically applicable pressures have shown a great constancy of the slide coefficient consistent with relation (2). Therefore, the relation (2) can be rewritten as, $$p_{dh} = p_c \eta^{Sh/4F} \quad (4)$$

where $p_{dh}$ is the pressure in a sample at a distance h from the face of the top punch. This relation allows to predict the pressure at any particular cross-section of the pressed compact once the sliding coefficient is known.

The non-uniform pressure distribution (4) creates non-homogeneous density of the compact along the direction of pressing. Despite the great technical importance of the density-pressure dependence, not much attention has been devoted to that aspect with relatively few papers reporting mainly results of direct density measurements (see Van Grenou). Such measurements are subjected to considerable errors that preclude any generalized description of the phenomenons accompanying the compaction process.

It has been determined (see Gasiorek et al.) that the density distribution along the height of the compact is linear. Thus, the apparent density measured at the half height of the compact, h=H/2, is equal to an average apparent density of the whole compact. The pressure $p_r$ at that height, called a reduced pressure, can be found from (4) to be:

$$p_r = p_c \eta^{SH/8F} \tag{5}$$

An introduction of the reduced pressure concept, $p_r$, allows one to determine the compaction characteristic which does not depend on the SH/4F quantity. In addition, it could be shown that the above compaction characteristic for die pressing is identical as the compaction characteristic obtained for isostatic pressing process.

An extensive experimental investigation has indicated a logaritmic functional dependence between the reduced pressure and the density, $$|\log|\log \rho_{ra}|| = f(\log p_r) \tag{6}$$

where 92 $_{ra}$ is an average relative density of a given sample. Furthermore, the functional relation, f, has been determined to be linear, $$|\log|\log \rho_{ra}|| = -\alpha \cdot \log\left(\frac{p_r + p_o}{p_o}\right) + |\log|\log \rho_{rp}||. \tag{7}$$

Here, $\alpha$—compactibility coefficient,
$p_o$—gravitational pressure of a powder,
$\rho_{rp}$—relative bulk density of a powder.

The expression (7) can be transformed to $$\rho_{ra} = \rho_{rp}^{\left(\frac{p_o}{p_r + p_o}\right)^\alpha} \tag{8}$$

Substituting in (8) for $p_r$ the pressure at a given distance h from the face of the top punch given in (4), one gets an equation for density distribution along the height of a given sample, that is:

$$\rho_r = \rho_{rp}^{\left(\frac{p_o}{p_o + p_c\eta^{\frac{Sh}{4F}}}\right)^\alpha} \tag{9}$$

The direct objective of pressing is to produce from a loose powder an agglomerate body having a definite shape and strength that will preserve itself during ejection from a die, transportation and other technological operations prior to sintering, and during sintering itself. Generally, the whole set of parameters defining the mechanical strength of a compact is called a cohesiveness of an agglomerate.

The cohesiveness of a compact for transportation and other handling purposes can be estimated by various comparative tests such as tumbling methods or impact resistivity measurements. In automatic pressing, the major problem is associated with the appearance of cracks in compacts. It has been commonly observed that the majority of cracks found in compacts before and after sintering is created during the ejection of the compact from the die.

It has been established experimentally (see Gasiorek et al.) that the cracks developed during the ejection stage can be avoided if, for one-end pressing, the following inequality is satisfied:

$$P_f/F_1 < W_s \tag{10}$$

where
$P_f$—friction force between a compact and a die's wall,
$F_1$—lateral area of a compact,
$W_s$—compression strength of a compact.

The friction force is given by $$P_f = P_c(1 - \eta^{SH/4F}) \tag{11}$$

where $P_c$ is the total force applied to the top punch.

As described above, for a given powder and a given die the knowledge of the following parameters: slide coefficient, $\eta$, compactibility coefficient, $\alpha$, and cohesiveness, C, in addition to others easily measurable data is sufficient to determine major powder characteristics necessary for proper design of the compacting process to ensure most uniform density distribution and crack-free, highly accurate final product. The test procedure for obtaining the desired parameters is the subject of this invention.

SUMMARY OF THE INVENTION

This invention describes a uniform test procedure for determination of powder and green compact properties: slide coefficient, compactibility coefficient and cohesiveness. A simple compaction test in a test die allows prescribed measurements of applied forces and dimensions of the test compact. The test die is required to be made of a material identical to the material used for a production die. The compaction pressure for the test is required to be comparable with the compaction pressure in a production process. Based on these measurements, the slide coefficient and the compactibility coefficient of the tested powder could be computed. A separate crushing test of the test compact provides its compression strength. The compression strength and the previous measurements are used to compute the cohesiveness of the compact. If the cohesiveness has a magnitude greater than or equal to 1.0, the powder is classified as acceptable for a production of compacts. The test procedure could be used during the design of a production die to establish an optimum powder composition and proper shape of the die, and during production process to keep powder composition within a prescribed range.

A more detailed explanation of the invention is provided in the following description and claims, and is illustrated in the accompanying drawings.

DESCRIPTION OF THE PREFERRED EMBODIMENT

For a given powder and a given die, the knowledge of the slide coefficient, $\eta$, compactibility coefficient, $\alpha$, and cohesiveness, C, in addition to others easily measurable data is sufficient to determine major powder characteristics necessary for proper design of the compacting process to ensure most uniform density distribution and crack-free, highly accurate final product. A single test described by this invention is required to determine all the above coefficients and parameters.

Figure 1:
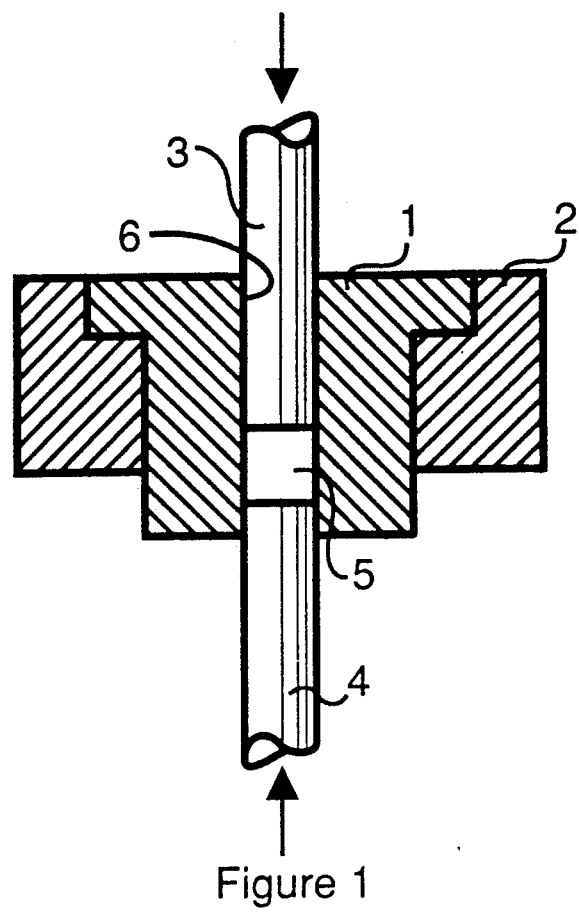
FIG. 1 is a cross-sectional view of the test apparatus according to the invention, showing a test compact in the process of being produced.
Figure 2:
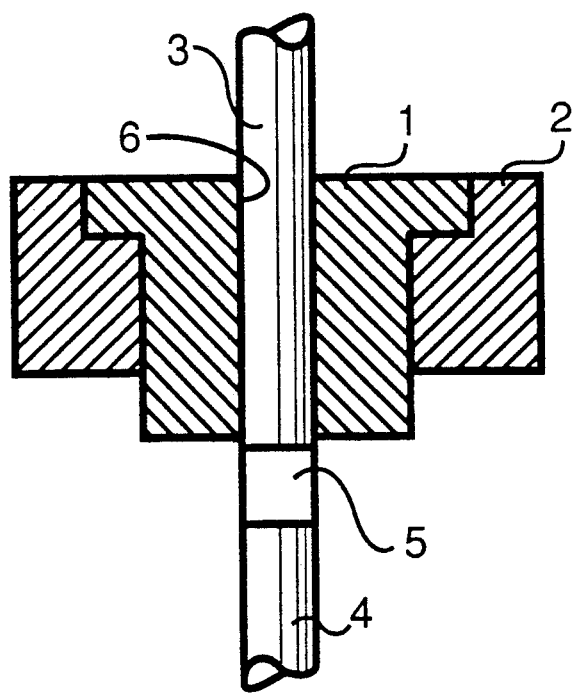
FIG. 2 is a cross-sectional view of the test apparatus of FIG. 1, showing the test compact being ejected from a die.

The test involves two steps illustrated on FIGS. 1 and 2. The first step (FIG. 1) comprises a pressing of a given powder in a test die 1 made of a material identical to the material used for a production die. The quality of the surface 6 of the test die should be comparable to that of a production die. The test die 1, fixed to apparatus 2, has a constant cross-section (circular in the present case although it could be arbitrary in shape) of the cavity and a vertical through opening. To perform the test, one end of the cavity (lower end) should be closed with punch 4 (second punch). A precisely measured amount of powder (mass $m_p$) should be placed in the cavity of the test die. The bulk density, $\rho_{rp}$, of the powder should be established by standard methods. The punch 3 (first punch) should close the cavity and compress the powder.

The maximum pressing pressure and the final density of the test sample 5 should be chosen such as to be comparable with those used in the industrial process for which the test is conducted. The amount of powder, $m_p$, should be chosen to achieve the final distance H greater than the maximum diameter of the cross-section of the test area.

During the compression, the test die 1 and the second punch 4 should be kept stationary. At the end of the pressing cycle and under load, the following should be recorded with high precision: force on the punch 3 ($P_c$), force on the punch 4 ($P_d$), distance between the faces of both punches (H), perimeter of the cross-section of the die's cavity (S), and the area of the cross-section of the die's cavity (F).

From the measured quantities, the slide coefficient, $\eta$, can be computed by solving the following equation:

$$\eta = (P_d/P_c)^{4F/SH}.$$

The average relative density, $\rho_{ra}$, can be computed from the following relation:

$$\rho_{ra} = (m_p/(FH))/\rho_{teo},$$

where the $\rho_{teo}$ is a teoretical density of a solid with a composition identical to that of the powder.

The compactibility coefficient, $\alpha$, can be computed by solving the following equation:

$$\alpha = (|\log|\log \rho_{rp}|| - |\log|\log \rho_{ra}||)/\log((P_r + P_o)/P_o),$$

where $\rho_{rp}$ is the relative (with respect to $\rho_{teo}$) bulk density of the powder, $p_o$ is the gravitational pressure of the powder, and $p_r$ is the reduced pressure computed from the following equation:

$$p_r = (P_c/F)\eta^{SH/8F}.$$

During the second step (FIG. 2), the compact should be removed from the test die in the direction of the pressing force on the first punch 3. In the present case, this is accomplished by moving the test die 1 up, in the direction of the first punch 3 while keeping the punches 3 and 4 stationary, although it could be accomplished by moving both punches, 3 and 4 down, in the direction of the pressing force on punch 3 while keeping the test die 1 stationary. A standard crashing test should be performed on the compact to determine its compression strength $W_s$, which is the maximum force necessary to destroy the sample.

The cohesiveness of the compact is computed by solving the following equation:

$$C = (W_s S H)/(P_c - P_d).$$

For a given powder and compacting process, the cohesiveness is acceptable only if C is greater than or equal to 1.0.

In a typical industrial application, the test described by this invention should be performed several times for a given powder with different amounts of additives to establish a graph that relates the slide coefficient to the amount of additives. An optimal composition of the powder should be adopted for the design of a production die and a compacting process. The same graph should be used during regular production of compacts to control the composition of the production powder. Each new mixture should be tested according to this invention and compared against the earlier established graph. The powder should be allowed for production of compacts only if its properties are within predetermined range of the graph, for which the die and the compacting process are designed.

Although the invention has been described in its preferred form with certain degree of particularity, it will be understood that the present disclosure of the preferred embodiment has been made only by way of an example and that various changes may be resorted to without departing from the true spirit and scope of the invention as herein after claimed. It is intended that the patent shall cover, by suitable expression in the appended claims, whatever features of patentable novelty exist in the invention disclosed.

I claim:

1. A method of determining whether a given powder is suitable for producing pressed powder compacts, comprising the steps of:
   providing a die having first and second ends, a constant cross-sectional area F, and a perimeter S;
   providing a first punch that tightly fits within the first end of the die;
   providing a second punch that tightly fits within the second end of the die;
   closing the second end of the die by inserting the second punch into the second end of the die;
   placing powder within the die;
   inserting the first punch into the first end of the die and compressing the powder while maintaining the second punch stationary to form a compact, the force on the first punch being identified as $P_c$, the force on the second punch being identified as $P_d$, and the distance between the first and the second punches being identified as H;

measuring $P_c$, $P_d$, H, S, and F while the compact is under load;

removing the compact from the die in the direction of force on the first punch;

crushing the compact outside the die, the pressure force needed to crush the compact being identified as $W_s$;

calculating the cohesiveness of the compact by solving the following equation:

$$C = (W_s SH)/(P_c - P_d)$$

accepting the powder for use in production only if C is greater than or equal to 1.0.

2. The method of claim 1, wherein the powder is metallic.

3. The method of claim 1, wherein the powder is nonmetallic.

4. The method of claim 1, wherein the powder is a mixture of metallic and nonmetallic constituents.

5. The method of claim 1, wherein the die has a circular cross-sectional area.

6. The method of claim 1, wherein the die is made of the same material as a die used to produce parts on a production basis.

7. The method of claim 1, wherein the compact is removed from the die by moving the die relative to the punches towards the first punch.

8. A method of controlling the composition of powder used in pressed powder compacts, comprising the steps of:

providing a die having first and second ends, a constant cross-sectional area F, and a perimeter S;

providing a first punch that tightly fits within the first end of the die;

providing a second punch that tightly fits within the second end of the die;

closing the second end of the die by inserting the second punch into the second end of the die;

placing powder within the die;

inserting the first punch into the first end of the die and compressing the powder while maintaining the second punch stationary to form a compact, the force on the first punch being identified as $P_c$, the force on the second punch being identified as $P_d$, and the distance between the first and the second punches being identified as H;

measuring $P_c$, $P_d$, H, S, and F while the compact is under load;

calculating the slide coefficient of the powder by solving the following equation:

$$\eta = (P_d/P_c)^{4F/SH};$$

providing powder samples, each having different amounts of additives;

calculating the slide coefficient of each sample;

plotting a graph of slide coefficient versus powder composition;

providing a proposed powder sample;

calculating the slide coefficient of the proposed powder sample;

adjusting the composition of the proposed powder sample to produce a calculated slide coefficient falling within a predetermined range of the graph.

9. The method of claim 8, wherein the powder is metallic.

10. The method of claim 8, wherein the powder is nonmetallic.

11. The method of claim 8, wherein the powder is a mixture of metallic and nonmetallic constituents.

12. The method of claim 8, wherein the die has a circular cross-sectional area.

13. The method of claim 8, wherein the die is made of the same material as a die to be used for producing parts on a production basis.

* * * * *